United States Patent [19]

Linder

[11] Patent Number: 5,188,617
[45] Date of Patent: Feb. 23, 1993

[54] APPARATUS AND A METHOD FOR TAKING SAMPLES FROM GUM POCKETS

[75] Inventor: Lars Linder, Stockholm, Sweden

[73] Assignee: Triple L. Laboratories AB, Stockholm, Sweden

[21] Appl. No.: 598,168

[22] Filed: Oct. 16, 1990

[30] Foreign Application Priority Data

Oct. 17, 1989 [SE] Sweden .................. 8903422

[51] Int. Cl.⁵ ........................................... A61M 5/00
[52] U.S. Cl. .................. 604/232; 604/239; 604/229; 604/117; 433/72; 433/80
[58] Field of Search .......... 604/232, 117, 272–274, 604/187, 218, 239, 229; 435/72, 75, 81, 80

[56] References Cited

U.S. PATENT DOCUMENTS

| | | | |
|---|---|---|---|
| 1,125,887 | 1/1915 | Schimmel | 604/239 X |
| 1,331,271 | 2/1920 | MacGregor | 604/239 |
| 2,098,524 | 11/1937 | Smith | 604/229 X |
| 2,526,365 | 10/1950 | Jorgensen | 604/229 |
| 2,554,744 | 5/1951 | Jorgensen | 604/229 |
| 2,668,535 | 2/1954 | Jorgensen | 604/229 |
| 2,731,964 | 1/1956 | Emrich | 604/232 X |
| 2,922,420 | 1/1960 | Cheng | 604/272 |
| 2,952,256 | 9/1960 | Meader et al. | 604/272 |
| 3,045,674 | 7/1962 | Goldberg | 604/229 X |
| 3,092,108 | 6/1963 | Friedman | 604/232 X |
| 3,340,872 | 9/1967 | Cox | 604/229 |
| 4,184,490 | 1/1980 | Jacklick | 604/224 |
| 4,276,880 | 7/1981 | Malmin | 604/264 X |
| 4,364,730 | 12/1982 | Axelsson | 433/141 |
| 4,381,779 | 5/1983 | Margulles | 604/202 |
| 4,629,454 | 12/1986 | Grier | 604/229 |
| 4,645,491 | 2/1987 | Evans | 604/158 |
| 4,707,450 | 11/1987 | Nason . | |
| 4,758,234 | 7/1988 | Orentreich et al. | 604/232 |
| 4,760,847 | 8/1988 | Vaillancourt | 606/185 |
| 4,768,952 | 9/1988 | Loewenthal | 433/72 |
| 4,993,941 | 2/1991 | Meita et al. | 433/80 |
| 5,129,888 | 7/1992 | Bidoia | 604/240 |

FOREIGN PATENT DOCUMENTS 1418337 12/1975 Canada .

Primary Examiner—John D. Yasko
Assistant Examiner—Mark O. Polutta
Attorney, Agent, or Firm—Paul & Paul

[57] ABSTRACT

An apparatus for taking samples from gum pockets, including a holder (1) for an ampoule (3) detachably inserted therein, a manually operated element (2) cooperating with the holder for reducing the space in the ampoule, so that liquid contained therein will be fed out through a cannula (4) connected to the holder, the cannula being intended to be inserted in a gum pocket. The apparatus is provided with means for restoring at least partly the space in the ampoule for feeding a mixture of sample and liquid into the ampoule.

1 Claim, 1 Drawing Sheet

APPARATUS AND A METHOD FOR TAKING SAMPLES FROM GUM POCKETS

DESCRIPTION

1. Technical field

The present invention relates to an apparatus for taking samples from gum pockets, comprising a holder for an ampoule detachably inserted therein, a manually operated element cooperating with the holder for reducing the space in the ampoule, such that liquid contained therein will be fed out through a cannula connected to the holder, which cannula is intended to be inserted in a gum pocket.

The invention also relates to an ampoule for use in such an apparatus and to a method of taking samples.

Periodontitis is a bacteriologically conditioned infectious disease involving loss of connective tissue and jaw bone and as a result of which the tooth will loose its hold in the jaw bone so that eventually it will be lost. The disease exists in three forms, i.e. prebuberty, juvenile and adult periodontitis. Either the entire set of teeth is affected or just the occasional tooth. Certain immunodeficiency diseases may cause rapidly developing, severe periodontitis. Individuals whose leucocyte or macrophage function is impaired often get severe periodontitis. Other diseases which may lead to an increased risk of periodontitis are diabetes, ulcerous colitis, and Chron's disease. However, in the case of periodontitis, the factors behind it are often unknown.

The normal bacterial flora in the gum pocket comprises about 200 species. Some few of these are considered to be pathogens in the case of periodontitis:

1. The black-pigmented Bacteroides species: *Bacteroides gingivalis* and *Bacteroides intermedius*,
2. *Actinobacillus actinomycetemcomitans*; escpecially in the case of juvenile periodontitis,
3. Capnocytophaga; especially in the case of periodontitis in young diabetics, and
4. Spirochaetes; pathogenic especially in the case of the gum disease acute necrotizing gingivitis.

There are some indications for obtaining a bacteriological diagnosis by taking samples from a gum pocket, such as to estimate the risk of development or continued development of periodontitis, to judge the result of the methods of treatment used, to analyse cases which are difficult to treat, to find out the causes in cases of rapidly progressing periodontitis, and to test the sensitivity of pathogenic bacteria to antibiotics in cases where antibiotics are to be used.

2. Prior art

The method of taking bacteriological samples from a gum pocket most frequently used today implies inserting 1-3 paper points in the pocket. After about 10 seconds the paper points will be removed and they will then be transferred to a special semi-solid transport medium in a bottle and forwarded to a bacteriological laboratory. In the laboratory, anaerobic culturing will then be carried out on various selective bacteriological media, and the share of *B gingivalis*, *B intermedius*, *Actinobacillus actinomycetemcomitans*, Capnocytophaga bacteria and other periodontitis pathogens of the total bacterial flora is determined.

Other methods of taking samples imply collecting bacteria from a gum pocket by means of dental calculus instruments and transferring the bacteria to a transport medium which will then be forwarded to a bacteriological laboratory.

The risk of periodontitis is estimated on the bases of the presence of certain pathogens or on the basis of percentage share of certain pathogens of the total flora. In the future the risk of periodontitis is likely to be estimated also on the basis of other criteria, such as specific enzyme activities in the gum pocket, the local leucocyte activity or the local immunological defence. For similar criteria to be used, a carefully standardized method of taking samples is a condition.

DESCRIPTION OF THE INVENTION

The problem to be solved by the present invention is to improve previously known devices and methods of taking samples from gum pockets, which problem is solved by the apparatus according to the invention being provided with the features stated in the characterizing portions of the claims.

Advantages of the invention to be mentioned are:

1. Sensitive anaerobic bacteria which will die when in contact with the oxygen of the air are prevented from getting into contact with the air:
2. Components in the gum pocket other than pathogenic bacteria, such as various enzymes and immunological defence components, may be determined;
3. It is possible to check that the sample is taken form a predetermined depth of the pocket, meaning that repeated samples may be taken from the same depth of pocket;
4. Since the taking of samples is carried out in a simple way and by the use of simple means, also less experienced personnel will be able to take relevant samples; and
5. The risk of infection for dental service personnel is reduced.

PREFERRED EMBODIMENT

Figure 1:
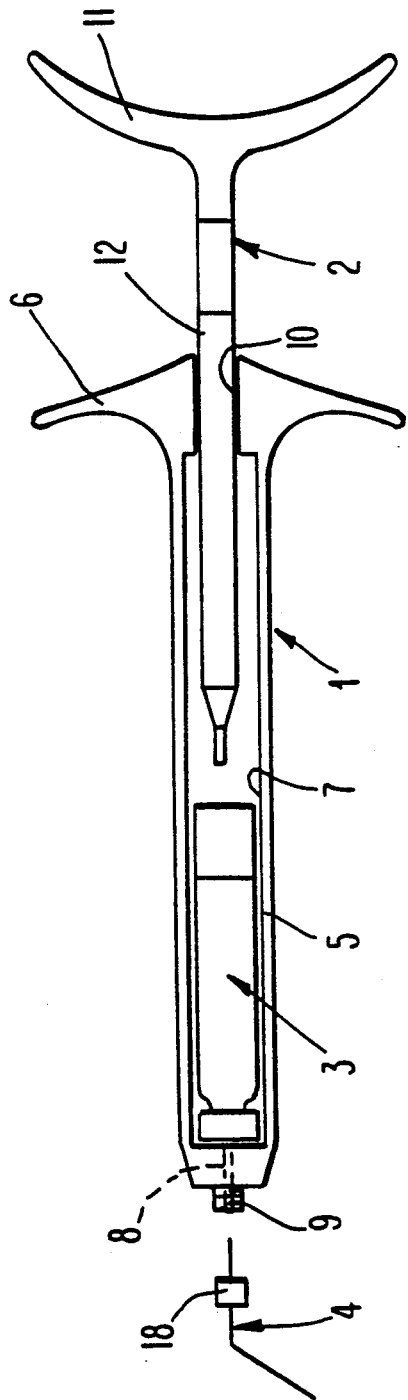
FIG. 1 is a schematic side view of the apparatus according to the invention.
Figure 3:
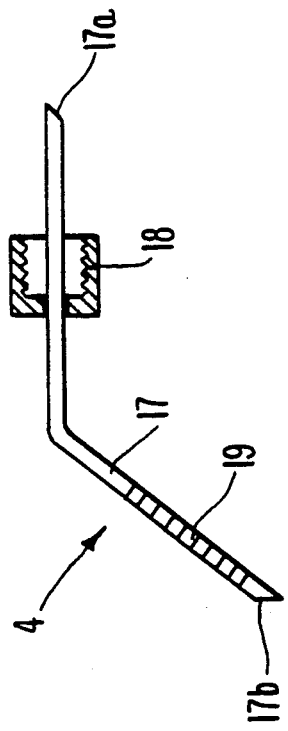
FIG. 3 is a schematic side view, partly in section and on an enlarged scale, showing a cannula included in the apparatus according to FIG. 1.
Figure 2:
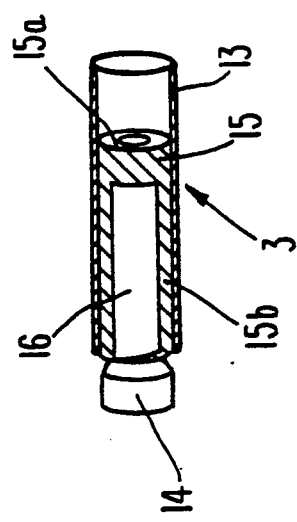
FIG. 2 is a schematic perspective view, partly in section, showing an ampoule included in the apparatus according to FIG. 1.

In FIG. 1 there is shown an apparatus according to the invention comprising four main parts, i.e. a holder 1, a manually operated element 2 cooperating with the holder 1, an ampoule 3 intended to be detachably retained in the holder, and a cannula 4 intended to be connected with the holder 1.

The holder 1 consists of an elongated tube 5 having a handle 6 and a slot 7 in the envelope surface of the tube, the slot extending substantially along the full length of the tube. The tube 5 is provided with a hole 8 at one end, which hole is surrounded by a thread 9, and a larger, slotted hole 10 at the other end.

The element 2 consists of a rod 12 provided with a handle 11, the rod having a circular cross section and a reduced diameter at the end facing away from the handle 11. The rod 12 fits into the hole 10 of the holder, the hole guiding the rod as it moves into and out of the tube 5. The element 2 and the holder 1 may consist of, for example, the main parts of a conventional syringe.

The ampoule 3 consists of a rigid tube, such as a cylindrical glass tube 13, which is sealed at one end by a body 14 comprising a diaphragm made from, for example, butyl rubber, and a cover, such as a cylindrical sleeve 15, which is inserted in the glass tube 13 and the outer diameter of which is equal to or somewhat larger than the inner diameter of the glass tube, such that it is displaceable in the glass tube and seals against the inner walls thereof. The sleeve 15 is made from an elastic material, such as rubber, and comprises a cylindrical end wall 15a and a tubular side wall 15b. Between the body 14 and the sleeve 15 there is formed a liquidproof space 16, in which there is room for a small volume of sampling liquid, such as 30–100 $\mu$l. The diameter of the ampoule 3 is adapted to the diameter of the tube 5 and the size of the slot 7 such that the ampoule may be inserted in and retained inside the tube 5 but may be removed therefrom through the slot 7 in one simple operation.

The cannula 4 consists of a tube 17, which is curved at an angle of, for example, 45°. On the outside of the tube 17 there is attached a sleeve 18 with an internal thread. One end 17a of the tube is pointed. The other end 17b of the tube is provided with a rounded edge and/or is blunt. A scale 19 suitably graduated in mm is indicated on the tube 17 from the end 17b towards the bend of the tube. The cannula 4 is intended to be mounted on the holder 1 by screwing the thread of the sleeve 8 onto the thread 9.

Prior to the taking of samples, the ampoule 3 containing sampling liquid is inserted in the holder 1 to the position shown in FIG. 1 in which the body 14 is located adjacent to the hole 8 of the tube 5. The cannula 4 is then screwed onto the holder 1. The pointed end 17a of the cannula will penetrate the diaphragm in the body 14 and is inserted in the space 16 in the ampoule 3. Before then, the rod 12 which is inserted in the holder i should have been brought to bear against the end wall 15a of the sleeve 15.

When samples are to be taken by means of the apparatus according to the invention, the cannula 4 is brought to the bottom of the gum pocket, and the depth of the pocket may then be read on the scale 19 of the cannula. The sampling liquid is carefully pressed out into the pocket through the cannula 4 in that the sleeve 15 is compressed by the rod 12 while the operator presses the handles 6 and 11 against each other by means of the fingers of one hand. At least part of the sampling liquid will then be aspirated together with the contents of the gum pocket into the sleeve 15 of the ampoule 3, which takes place in that the sleeve 15 resumes its original shape when the operator releases the pressure on the rod 12. The procedure may be repeated by means of careful pumping movements. The ampoule 3 is then removed from the holder 1 and forwarded to a bacteriological laboratory, where sample and liquid will be pressed out of the sleeve 15 by means of an apparatus similar to the one described above. However, the cannula 4 does not have to be graduated or curved. The sample will then be subject to a bacteriological analysis by means of anaerobic culturing in the conventional way and/or will be analyzed with respect to various enzyme activities, immunoglobulins and other serum proteins. The composition of the sampling liquid must be such that the viability of sensitive anaerobic bacteria will be maintained during the transport of the ampoule 3 to the laboratory. Further, in order to maintain the proportion of the various species included, the liquid must contain substance which will prevent growth of the bacteria during the transport.

While only one embodiment of the present invention has been described above and shown on the drawing, it will be understood that the invention is not limited to said embodiment but only by what is stated in the claims.

I claim:

1. An apparatus for taking samples from gum pockets, including;
    a holder and an ampoule detachably inserted therein,
    a cannula connected to the holder and insertable at one end into the ampoule and at the other end into a gum pocket, said cannula having a graduated scale that indicates the distance that the cannula has been inserted into the gum pocket, said cannula forming an angle of from approximately 30° to about 60° with respect to the longitudinal axis of said holder;
    said ampoule comprising a rigid tube sealed at one end by a penetrable diaphragm, and at the other end by an elastic cover inserted into the rigid tube such that it is displaceable therein and seals against the inner walls thereof thereby forming a liquidproof space with said penetrable diaphragm,
    a manually operated element cooperating with the holder and adapted to displace the elastic cover whereby liquid contained in said space will be fed out through said cannula, and liquid external to said space in said gum pocket can be drawn in through said cannula and said diaphragm for retention in said space.

* * * * *